US010039691B2

(12) United States Patent
Von Hollen et al.

(10) Patent No.: US 10,039,691 B2
(45) Date of Patent: Aug. 7, 2018

(54) VIBRATORY POSITIVE EXPIRATORY PRESSURE DEVICE

(75) Inventors: Dirk Ernest Von Hollen, Clark, NJ (US); Christopher John Brooks, Glen Cove, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1444 days.

(21) Appl. No.: 13/825,263

(22) PCT Filed: Sep. 15, 2011

(86) PCT No.: PCT/IB2011/054038
§ 371 (c)(1),
(2), (4) Date: Mar. 20, 2013

(87) PCT Pub. No.: WO2012/038864
PCT Pub. Date: Mar. 29, 2012

(65) Prior Publication Data
US 2013/0184619 A1    Jul. 18, 2013

Related U.S. Application Data

(60) Provisional application No. 61/384,745, filed on Sep. 21, 2010.

(51) Int. Cl.
| | |
|---|---|
| *A61H 23/00* | (2006.01) |
| *A61M 16/00* | (2006.01) |
| *A61M 16/20* | (2006.01) |
| *A63B 23/18* | (2006.01) |
| *A63B 21/00* | (2006.01) |

(52) U.S. Cl.
CPC ............. *A61H 23/00* (2013.01); *A61M 16/00* (2013.01); *A61M 16/0006* (2014.02);
(Continued)

(58) Field of Classification Search
CPC ..................... A61M 15/0005–15/0008; A61M 15/0013–15/002; A61M 16/00;
(Continued)

(56) References Cited

U.S. PATENT DOCUMENTS 3,699,964 A * 10/1972 Ericson ...................... A61F 5/44
128/912
3,906,989 A * 9/1975 Lamb ................... B67D 1/0832
137/320

(Continued)

FOREIGN PATENT DOCUMENTS

| CN | 1330961 A | 1/2002 |
|---|---|---|
| CN | 2580961 Y | 10/2003 |

(Continued)

OTHER PUBLICATIONS

H. Douglass et al; "In the World of Airways Clearance: Physiology, Devices, Evidence and the Future", The Buyers' Guide to Respiratory Care Products, pp. 1-18.

*Primary Examiner* — Rachel T Sippel
(74) *Attorney, Agent, or Firm* — Michael W. Haas

(57) ABSTRACT

A method of providing airway clearance therapy to a patient includes receiving an expiratory airstream from the patient in a chamber, causing a back pressure to be created in the chamber (10) in response to receiving the expiratory airstream, causing a one-way valve, such as a magnetic duckbill valve (26), located downstream of the chamber to open only in response to the back pressure being at least equal to a certain predetermined level, causing a vibratory effect to be generated downstream of the one-way valve, for example using a vibratory ball check valve (32), when the one-way valve is open and in response to the expiratory air-stream passing therethrough, and delivering a percussive sensation to the patient through the chamber responsive to the vibratory effect.

18 Claims, 4 Drawing Sheets

(52) U.S. Cl.
CPC ........ *A61M 16/209* (2014.02); *A61M 16/208* (2013.01); *A63B 21/00196* (2013.01); *A63B 23/18* (2013.01)

(58) Field of Classification Search
CPC ............... A61M 16/0006–16/0009; A61M 16/20–16/201; A61M 16/206–16/208; A61M 39/22; A61M 39/227; A61M 39/24; A61M 2039/2406; A61M 2039/242–2039/2486; A61H 23/00; A61H 23/04; A63B 21/00196; A63B 21/008; A63B 23/18–23/185
See application file for complete search history.

(56) References Cited

U.S. PATENT DOCUMENTS

| | | | |
|---|---|---|---|
| 3,908,987 A * | 9/1975 | Boehringer | A63B 23/18 482/13 |
| 6,176,235 B1 | 1/2001 | Benarrouch | |
| D440,651 S | 4/2001 | Foran et al. | |
| 6,581,598 B1 | 6/2003 | Foran et al. | |
| 6,726,598 B1 * | 4/2004 | Jarvis | A63B 23/18 128/200.24 |
| 7,166,128 B1 * | 1/2007 | Persson | A61F 2/203 623/9 |
| 2003/0159697 A1 * | 8/2003 | Wallace | A61M 16/00 128/204.26 |
| 2008/0110451 A1 | 5/2008 | Dunsmore | |
| 2008/0110455 A1 | 5/2008 | Dunsmore | |
| 2008/0142013 A1 * | 6/2008 | Hallett | A61M 16/06 128/205.24 |

FOREIGN PATENT DOCUMENTS

| | | |
|---|---|---|
| CN | 201329062 Y | 10/2009 |
| CN | 101622036 A | 1/2010 |
| EP | 1464357 A1 | 10/2004 |
| WO | 198903707 A1 | 5/1989 |
| WO | 2008122045 A1 | 10/2008 |

* cited by examiner

VIBRATORY POSITIVE EXPIRATORY PRESSURE DEVICE

The present invention relates to treatment of lung diseases, such as Cystic Fibrosis, wherein mucus secretions build up in the lungs, and in particular to a vibratory positive expiratory pressure (PEP) device for use in clearing the lungs of such secretions.

A number of respiratory conditions are known in which the patient experiences large build-ups of mucus in the lungs. One such respiratory condition is Cystic Fibrosis. Cystic Fibrosis is an inherited, progressively debilitating disease wherein a defective gene causes impaired mucociliary transport in the lungs, leading to chronic pulmonary obstruction, inflammation and infection. It is thus important for people suffering from such conditions to clear their airways, and such people spend a significant amount of time attempting to do so.

A number of airway clearance techniques are well known. Such techniques include manual chest physiotherapy (CPT), postural drainage, breathing exercises and coughing. Many people will also use an airway clearance device to assist them with the task of clearing their airways. A number of such devices are known. One type of airway clearance device is known as a positive expiratory pressure (PEP) device. A PEP device is typically a small hand-held device having a mouthpiece and a chamber that includes a one-way valve that allows air to flow in easily during inhalation but that creates a resistance during exhalation. To clear his or her lungs using a PEP device, the patient breathes in and out through the device several times and then huffs to remove the loosened mucus. Another, related airway clearance device is known as a vibrating (or vibratory) positive expiratory pressure device. Vibrating (or vibratory) PEP devices work in the same way as PEP devices except that they also provide vibration to the patient's lungs to help shake the mucus loose.

While such techniques and devices have been successful in treating respiratory conditions such as Cystic Fibrosis, there is room for improvement in this area.

In one embodiment, a positive expiratory pressure device is provided that includes a chamber structured to receive an expiratory airstream of a patient, the chamber having a fluid pathway passing therethrough, a magnetic duckbill valve provided along the fluid pathway, the magnetic duckbill valve having a first wall supporting a number of first magnets having a first polarity and a second wall supporting a number of second magnets having a second polarity opposite the first polarity, the first magnets and the second magnets being configured to create a resistive cracking force in the magnetic duckbill valve wherein the magnetic duckbill valve is structured to open only in response to at least a certain back pressure being created in the chamber, and a vibratory ball check valve provided along the fluid pathway downstream of the magnetic duckbill valve.

In another embodiment, a positive expiratory pressure device is provided that includes a chamber structured to receive an expiratory airstream of a patient, a one-way valve provided downstream of the chamber, wherein the one-way valve is structured to open only in response to at least a certain back pressure being created in the chamber, and a vibratory ball check valve provided downstream of the one-way valve, wherein the chamber, the one-way valve and the vibratory ball check valve are provided along a linear fluid flow pathway.

In still another embodiment, a method of providing airway clearance therapy to a patient is provided that includes receiving an expiratory airstream from the patient in a chamber, causing a back pressure to be created in the chamber in response to receiving the expiratory airstream, causing a one-way valve located downstream of the chamber to open only in response to the back pressure being at least equal to a certain predetermined level, causing a vibratory effect to be generated downstream of the one-way valve when the one-way valve is open and in response to the expiratory airstream passing therethrough, and delivering a percussive sensation to the patient through the chamber responsive to the vibratory effect.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
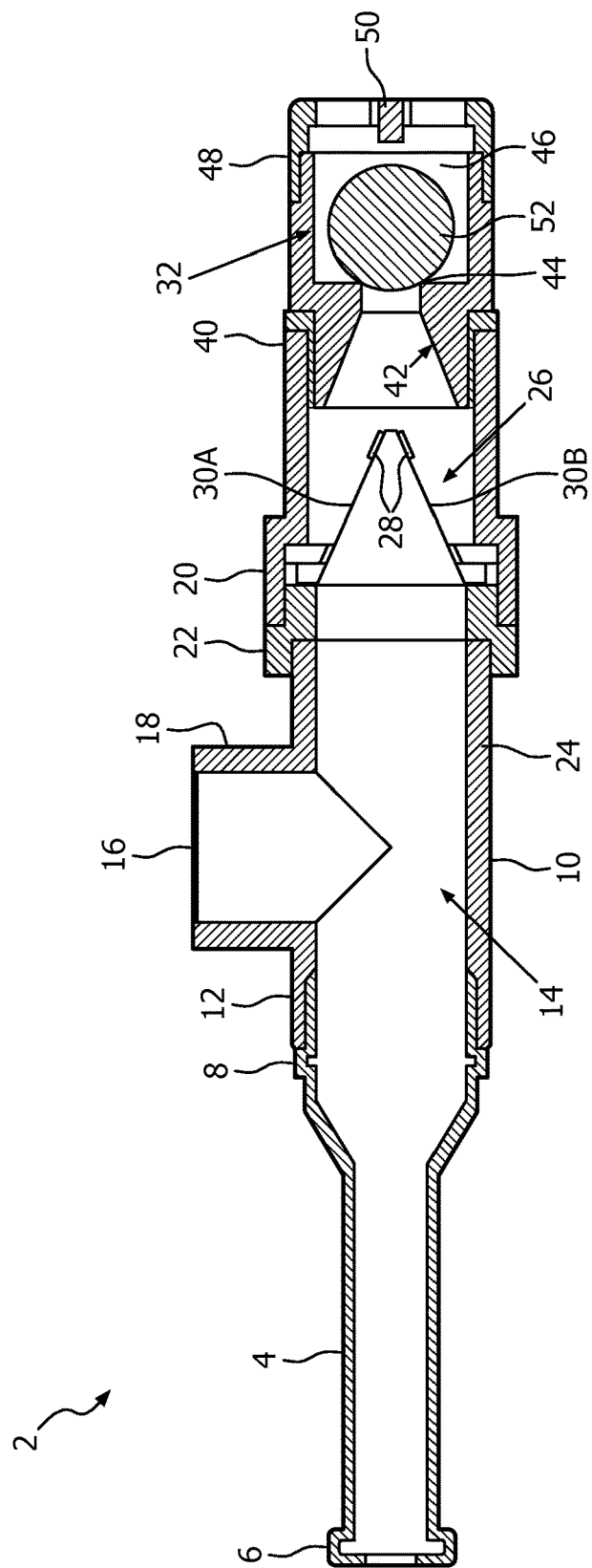
FIG. 1 is a schematic, cross-sectional diagram of vibratory positive expiratory pressure (PEP) device according to an exemplary embodiment of the present invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

Figure 2:
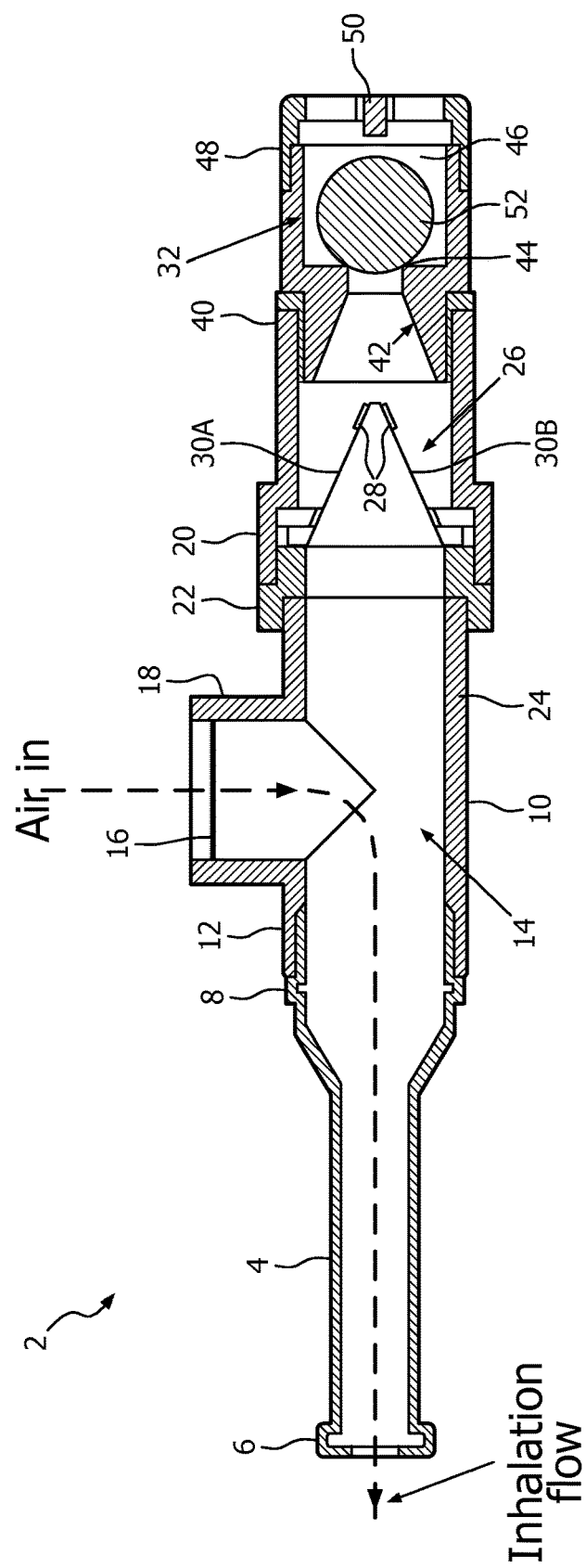
FIG. 2 is a schematic, cross-sectional diagram of the vibratory positive expiratory pressure (PEP) device of FIG. 1 showing the operation thereof during patient inhalation.

FIG. 1 is a schematic, cross-sectional diagram of vibratory positive expiratory pressure (PEP) device 2 according to an exemplary embodiment of the present invention. FIG. 2 is a schematic, cross-sectional diagram of vibratory PEP device 2 showing the operation thereof during inhalation by the patient, and FIG. 3 is a schematic, cross-sectional diagram of vibratory PEP device 2 showing the operation thereof during exhalation by the patient.

Vibratory PEP device 2 includes mouthpiece portion 4. Mouthpiece portion 4 is a patient interface that is structured to enable the patient to place his or her mouth on the first end 6 thereof and inhale and exhale through vibratory PEP device 2. In the exemplary embodiment, mouthpiece portion 4 is manufactured of injection molded plastic.

Vibratory PEP device 2 includes further includes air intake chamber 10, magnetic duckbill chamber assembly 20, and vibratory ball check valve assembly 32. The structure and function of each of air intake chamber 10, magnetic duckbill chamber assembly 20, and vibratory ball check valve assembly 32 is described in detail below.

Figure 3:
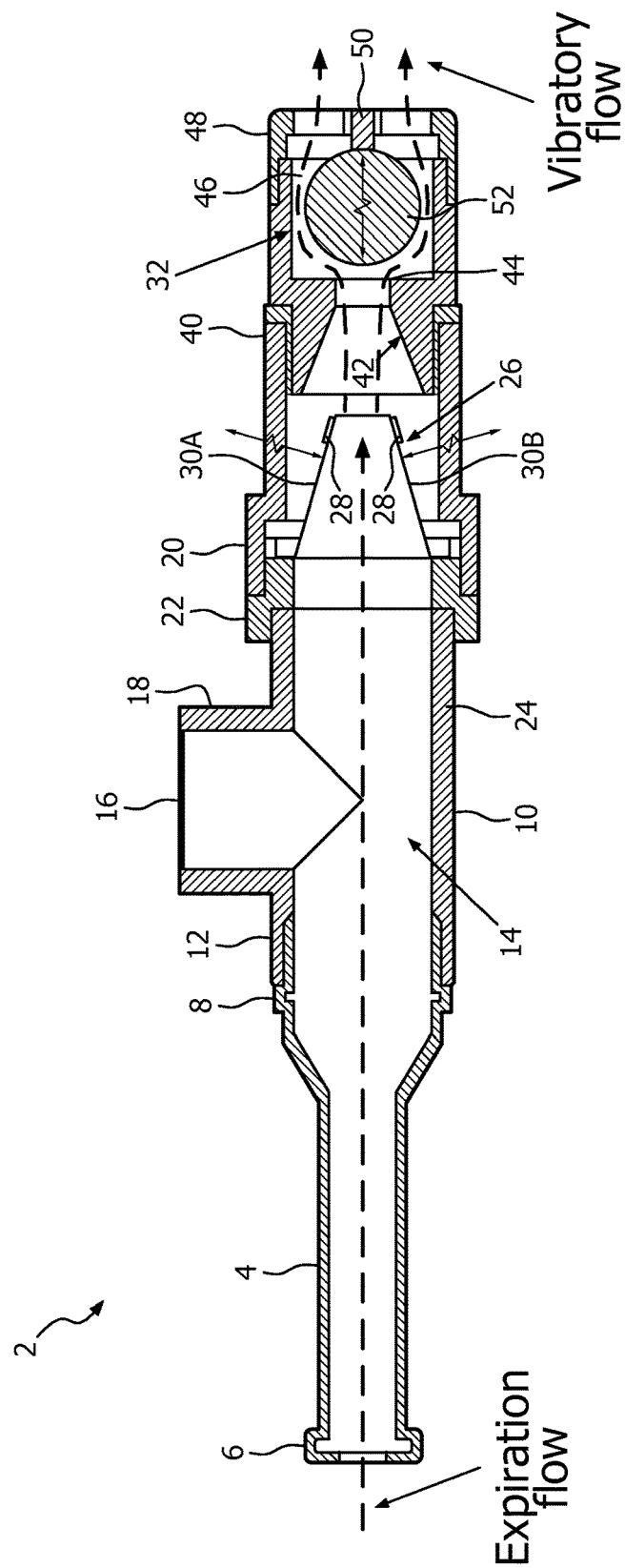
FIG. 3 is a schematic, cross-sectional diagram of the vibratory positive expiratory pressure (PEP) device of FIG. 1 showing the operation thereof during patient exhalation.

As seen in FIGS. 1-3, first end 12 of air intake chamber 10 is coupled to second end 8 of mouthpiece portion 4. Air intake chamber 10 comprises an inline check valve assembly that allows air to be entrained into longitudinal fluid pathway 14 of vibratory PEP device 2 when the patient inhales. In the exemplary embodiment, air intake chamber 10, like mouthpiece portion 4, is manufactured of injection molded plastic (in an alternative embodiment, air intake chamber 10 and mouthpiece portion 4 are molded as a single, integrated structure). In the illustrated embodiment, check valve 16 is provided in intake port tube 18 of air intake chamber 10. Intake port tube 18 is oriented perpendicular to longitudinal fluid pathway 14. In one particular, non-limiting embodiment, check valve 16 is a compliant elastomeric disc which will deform inward and crack under the vacuum pressure created by patient inhalation to allow air to freely flow into the patient's airways through air intake chamber 10 and mouthpiece portion 4 (FIG. 2). Upon patient exhalation (FIG. 3), the expiratory pressure will close check valve 16, seal air intake chamber 10, and create a positive pressure build up in air intake chamber 10. That positive pressure build-up in air intake chamber 10 will affect magnetic duckbill chamber assembly 20 and vibratory ball check valve assembly 32 of vibratory PEP device 2 in the manner described in detail below.

As seen in FIGS. 1-3, first end 22 of magnetic duckbill chamber assembly 20 is coupled to second end 24 of air intake chamber 10. Magnetic duckbill chamber assembly 20 retains and seals magnetic duckbill valve 26 to the air intake chamber 10. Magnetic duckbill valve 26 is a one-way duckbill valve that has a series of biased mini-magnets 28 fixed to the leading edges of each lip or wall 30A, 30B thereof (the magnets 28 fixed to wall 30A have a polarity that is opposite the polarity of the magnets 28 fixed to wall 30B). Magnets 28 create a controlled resistive cracking force in magnetic duckbill valve 26. That cracking force will (i) only allow magnetic duckbill valve 26 to snap open when sufficient back pressure (greater than a certain predetermined amount (i.e., a cracking pressure)) is achieved in air intake chamber 10 due to patient exhalation (FIG. 3), and (ii) cause magnetic duckbill valve 26 to quickly snap closed when the pressure in air intake chamber 10 drops (below the predetermined cracking pressure) at the end of patient exhalation. In the exemplary embodiment, magnets 28 are nickel plated neodymium magnets that are 2 mm in diameter and 1 mm thick, and that each have a max energy product of 37.46 megaGauss-Oersteds (MGOe). The sensation to the patient upon magnetic duckbill valve 26 opening is (i) a quick pressure drop or pop prior to initiating the actuation of vibratory ball check valve assembly 32 described in detail below, and (ii) a defined closure pressure at the end of patient exhalation. In the exemplary embodiment, the portions of magnetic duckbill chamber assembly 20 other than magnetic duckbill valve 26 are manufactured of injection molded plastic.

Figure 4:
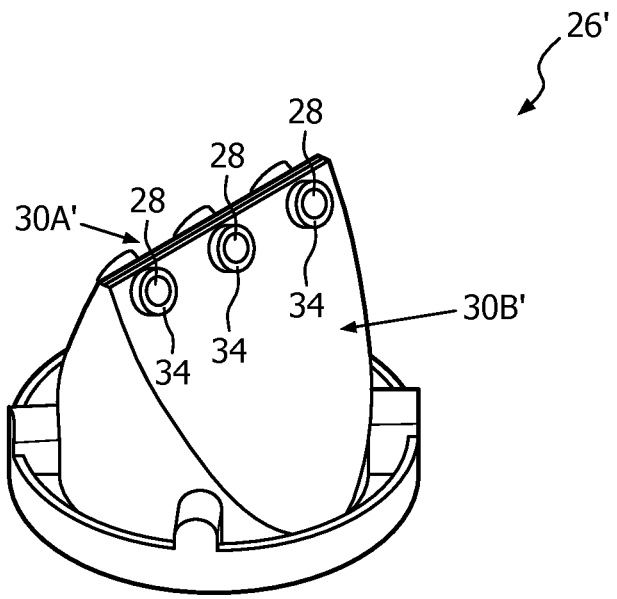
FIGS. 4 and 5 are isometric views of different embodiments of a magnetic duckbill valve that may form a part of the vibratory positive expiratory pressure (PEP) device of FIG. 1.

FIG. 4 is an isometric view of a particular, non-limiting example embodiment of magnetic duckbill valve 26, labeled as magnetic duckbill valve 26'. As seen in FIG. 4, each wall 30A', 30B' of magnetic duckbill valve 26' includes integral pockets 34 for retaining magnets 28 therein. In addition, each wall 30A', 30B' of magnetic duckbill valve 26' is a flat structure causing magnetic duckbill valve 26' to take the form of a straight taper valve.

Figure 5:
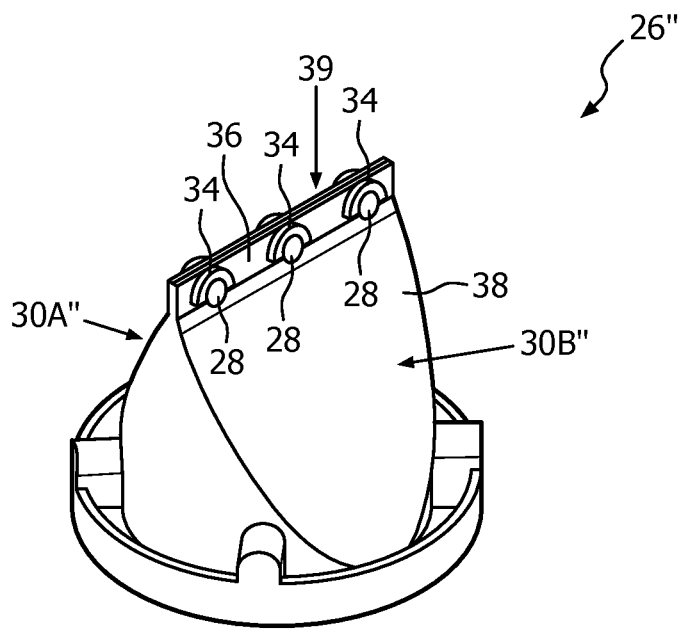

FIG. 5 is an isometric view of an alternative particular, non-limiting example embodiment of magnetic duckbill valve 26, labeled as magnetic duckbill valve 26". As seen in FIG. 4, each wall 30A", 30B" of magnetic duckbill valve 26" includes integral pockets 34 for retaining magnets 28 therein. In addition, each wall 30A", 30B" of magnetic duckbill valve 26" includes a flat, rectangular shaped angled portion 36 coupled to tapered main wall portion 38. When magnetic duckbill valve 26", the angled portions 36 engage one another and together form flat lipped sealing surface 39.

Vibratory PEP device 2 further includes vibratory ball check valve assembly 32 connected to second end 40 of magnetic duckbill chamber assembly 20. Vibratory ball check valve assembly 32 includes tapered (e.g., conically shaped) tuned air inlet 42, circular valve seat 44 at the end of air inlet 42, chamber 46, perforated cap element 48, snubber 50 (made of an elastomeric material such as rubber) incorporated into cap element 48, and spherical element 52 provided in chamber 46. In the exemplary embodiment, spherical element 52 is made of polypropylene. Air inlet 42 increases the velocity of the patient's exhaled breathe to displace spherical element 52 from valve seat 44 in response thereto (FIG. 3). As spherical element 52 is pushed off valve seat 44, a pressure drop occurs which creates a vacuum, the Bernoulli effect, and sucks the spherical element 52 back onto valve seat 44. Also, snubber 50 acts like a spring, which upon impact with spherical element 52 forces it back toward valve seat 44 (thus, snubber 50 works in conjunction with the vacuum to accelerate resealing of chamber 46). As the patient exhales into vibratory PEP device 2 and magnetic duckbill valve 26 is forced and held open, this process repeats a number of times and creates an oscillating vibratory effect which provides the patient with a percussive sensation through vibratory PEP device 2 that helps to dislodge mucus from the patient's airways. The vibration and percussive sensation will continue until exhalation ends and magnetic duckbill valve 26 snaps closed as a result of the pressure within air intake chamber 10 falling below the cracking pressure. In the exemplary embodiment, the components of vibratory ball check valve assembly 32 (other than spherical element 52 and internal rubber snubber 50) are manufactured of injection molded plastic.

Thus, vibratory PEP device 2 is a tool that can be used by patients, such as Cystic Fibrosis patients, to help clear their airways that provides both resistance and vibration during exhalation. The present invention may also be applied to airway clearance devices for Respiratory Drug Delivery (RDD) or Heat Rate Change (HRC), and may also be applied in nebulizers and other inhaler-type devices.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A positive expiratory pressure device, comprising:
a chamber structured to receive an expiratory airstream of a patient, the chamber having a fluid pathway passing therethrough;
a magnetic duckbill valve provided along the fluid pathway, the magnetic duckbill valve having a first wall supporting a number of first magnets having a first polarity and a second wall supporting a number of second magnets having a second polarity opposite the first polarity, the first magnets and the second magnets being configured to create a resistive cracking force in the magnetic duckbill valve wherein the magnetic duckbill valve is structured to open only in response to at least a certain back pressure being created in the chamber; and
a vibratory ball check valve provided along the fluid pathway downstream of the magnetic duckbill valve.

2. The positive expiratory pressure device according to claim 1, wherein the chamber comprises an air intake chamber having an air intake port oriented perpendicular to the fluid pathway, the air intake port having a check valve structured to permit only fluid flow into the air intake port.

3. The positive expiratory pressure device according to claim 2, further comprising a mouthpiece portion coupled to a first end of the air intake chamber, the magnetic duckbill valve being provided in magnetic duckbill valve assembly coupled to a second end of the air intake chamber.

4. The positive expiratory pressure device according to claim 2, wherein the fluid pathway is a longitudinal fluid pathway provided along a longitudinal axis of the positive expiratory pressure device.

5. The positive expiratory pressure device according to claim 3, wherein the vibratory ball check valve is provided as part of a vibratory ball check valve assembly, wherein a first end of the vibratory ball check valve assembly is coupled to an outlet end of the magnetic duckbill valve assembly, wherein the vibratory ball check valve assembly includes a tapered port provided at the first end thereof, a valve seat (44) provided at an end of the tapered port, a second chamber provided adjacent the valve seat (44), and a spherical element provided in the second chamber, the spherical element being structured to move within the second chamber and intermittently engage the valve seat (44).

6. The positive expiratory pressure devices according to claim 5, wherein the vibratory ball check valve assembly includes a snubber element positioned in the second chamber opposite the valve seat (44), wherein the spherical element is structured to intermittently engage the snubber element.

7. The positive expiratory pressure device according to claim 6, wherein the snubber element is made of an elastomeric material.

8. The positive expiratory pressure device according to claim 1, wherein the number of the first magnets is an integer greater than 1, and wherein the number of the second magnets is an integer greater than 1.

9. The positive expiratory pressure device according to claim 1, wherein each of the first magnets and each of the second magnets is a nickel plated neodymium magnet.

10. A positive expiratory pressure device, comprising:
a chamber structured to receive an expiratory airstream of a patient;
a one-way valve provided downstream of the chamber, wherein the one-way valve is structured to open only in response to at least a certain back pressure being created in the chamber; and
a vibratory ball check valve provided downstream of the one-way valve, wherein the chamber, the one-way valve and the vibratory ball check valve are provided along a linear fluid flow pathway 14), wherein the one-way valve is a magnetic duckbill valve having a first wall supporting a first magnet having a first polarity and a second wall supporting a second magnet having a second polarity opposite the first polarity, the first magnet and the second magnet being configured to create a resistive cracking force in the magnetic duckbill valve wherein the magnetic duckbill valve is structured to open only in response to the certain back pressure in the chamber being at least equal to a predetermined level.

11. The positive expiratory pressure device according to claim 10, wherein the chamber comprises an air intake chamber having an air intake port oriented perpendicular to the linear fluid flow pathway, the air intake porter having a check valve structured to permit only fluid flow into the air intake port.

12. The positive expiratory pressure device according to claim 10, wherein the one-way valve is provided in a valve assembly coupled to an end of the chamber, wherein the vibratory ball check valve is provided as part of a vibratory ball check valve assembly, wherein a first end of the vibratory ball check valve assembly is coupled to an outlet end of the valve assembly, wherein the vibratory ball check valve assembly includes a tapered port provided at the first end thereof, a valve seat (44) provided at an end of the tapered port, a second chamber provided adjacent the valve seat (44), and a spherical element provided in the second chamber, the spherical element being structured to move within the second chamber and intermittently engage the valve seat (44).

13. The positive expiratory pressure device according to claim 12, wherein the vibratory ball check valve assembly includes a snubber element positioned in the second chamber opposite the valve seat (44), wherein the spherical element is structured to intermittently engage the snubber element.

14. The positive expiratory pressure device according to claim 13, wherein the snubber element is made of an elastomeric material.

15. A method of providing airway clearance therapy to a patient, comprising:
receiving an expiratory airstream from the patient in a chamber;
causing a back pressure to be created in the chamber in response to receiving the expiratory airstream;
causing a one-way valve located downstream of the chamber to open only in response to the back pressure being at least equal to a certain predetermined level;
causing a vibratory effect to be generated downstream of the one-way valve when the one-way valve is open and in response to the expiratory airstream passing therethrough; and
delivering a percussive sensation to the patient through the chamber responsive to the vibratory effect, wherein the one-way valve is a magnetic duckbill valve having a first wall supporting a first magnet having a first polarity and a second wall supporting a second magnet having a second polarity opposite the first polarity, the first magnet and the second magnet being configured to create a resistive cracking force in the magnetic duckbill valve wherein the magnetic duckbill valve is structured to open only in response to the back pressure in the chamber being at least equal to the certain predetermined level.

16. The method according to claim 15, wherein the magnetic duckbill valve contributes to the vibratory effect when it snaps closed.

17. The method according to claim 15, wherein the causing the vibratory effect comprises causing a vibratory ball check valve located downstream of the one-way valve to create the vibratory effect.

18. The method according to claim 17, wherein the chamber, the one-way valve and the vibratory ball check valve are provided along a linear fluid flow pathway.

* * * * *